United States Patent [19]

Fletcher et al.

[11] Patent Number: 5,423,963
[45] Date of Patent: Jun. 13, 1995

[54] FOULING COMPENSATION IN AN OXYGEN ANALYZER

[75] Inventors: Kenneth S. Fletcher, Portsmouth, R.I.; Bradford E. Ross, Braintree, Mass.

[73] Assignee: The Foxboro Company, Foxboro, Mass.

[21] Appl. No.: 269,346

[22] Filed: Jun. 30, 1994

Related U.S. Application Data

[63] Continuation-in-part of Ser. No. 954,395, Sep. 30, 1992, Pat. No. 5,326,447.

[51] Int. Cl.⁶ .............................................. G01N 27/26
[52] U.S. Cl. .................... 204/153.17; 204/153.1; 204/401; 204/406; 204/412; 204/415; 204/431; 204/432
[58] Field of Search .............. 204/401, 406, 412, 415, 204/431, 432, 153.17, 153.1

[56] References Cited

U.S. PATENT DOCUMENTS

| | | | |
|---|---|---|---|
| 3,227,643 | 1/1966 | Okun et al. | 204/195 |
| 3,420,764 | 1/1969 | Schlein | 204/195 |
| 3,432,418 | 3/1969 | Kleiss | 204/195 |
| 3,857,771 | 12/1974 | Sternberg | 204/431 |
| 4,207,146 | 1/1980 | Kunke | 204/403 |
| 4,464,230 | 8/1984 | Langdon | 204/406 |
| 4,900,422 | 2/1990 | Bryan et al. | 204/415 |
| 5,016,201 | 5/1991 | Bryan et al. | 204/401 |
| 5,046,028 | 9/1991 | Bryan et al. | 204/401 |
| 5,098,547 | 3/1992 | Bryan et al. | 204/401 |
| 5,215,644 | 6/1993 | Ashikaga | 204/431 |

OTHER PUBLICATIONS

Smart, et al. In Situ Voltammetric Membrane Ozone Electrode, 1979, *Analytical Chemistry*, vol. 51, No. 14, pp. 2315 to 2319. No month available.

Michael L. Hitchman, Measurement of Dissolved Oxygen, 1978, Zurich, Switzerland, Chapters 4 and 5, pp. 59–123. No month available.

*Primary Examiner*—John Niebling
*Assistant Examiner*—Bruce F. Bell
*Attorney, Agent, or Firm*—Fish & Richardson

[57] ABSTRACT

A level of a chemical in a fluid is accurately measured by an analyzer having an electrode assembly separated from the fluid by a membrane. The electrode assembly is energized to provide a steady state signal and a pulsed signal, both of which indicate the level of chemical in the fluid, but with only the pulsed signal being substantially unaffected by fouling of the membrane. The pulsed signal and the steady state signal are used to determine a predicted value that the steady state signal will have in the absence of fouling. The predicted value is then used to correct the steady state current to compensate for fouling of the membrane.

47 Claims, 8 Drawing Sheets

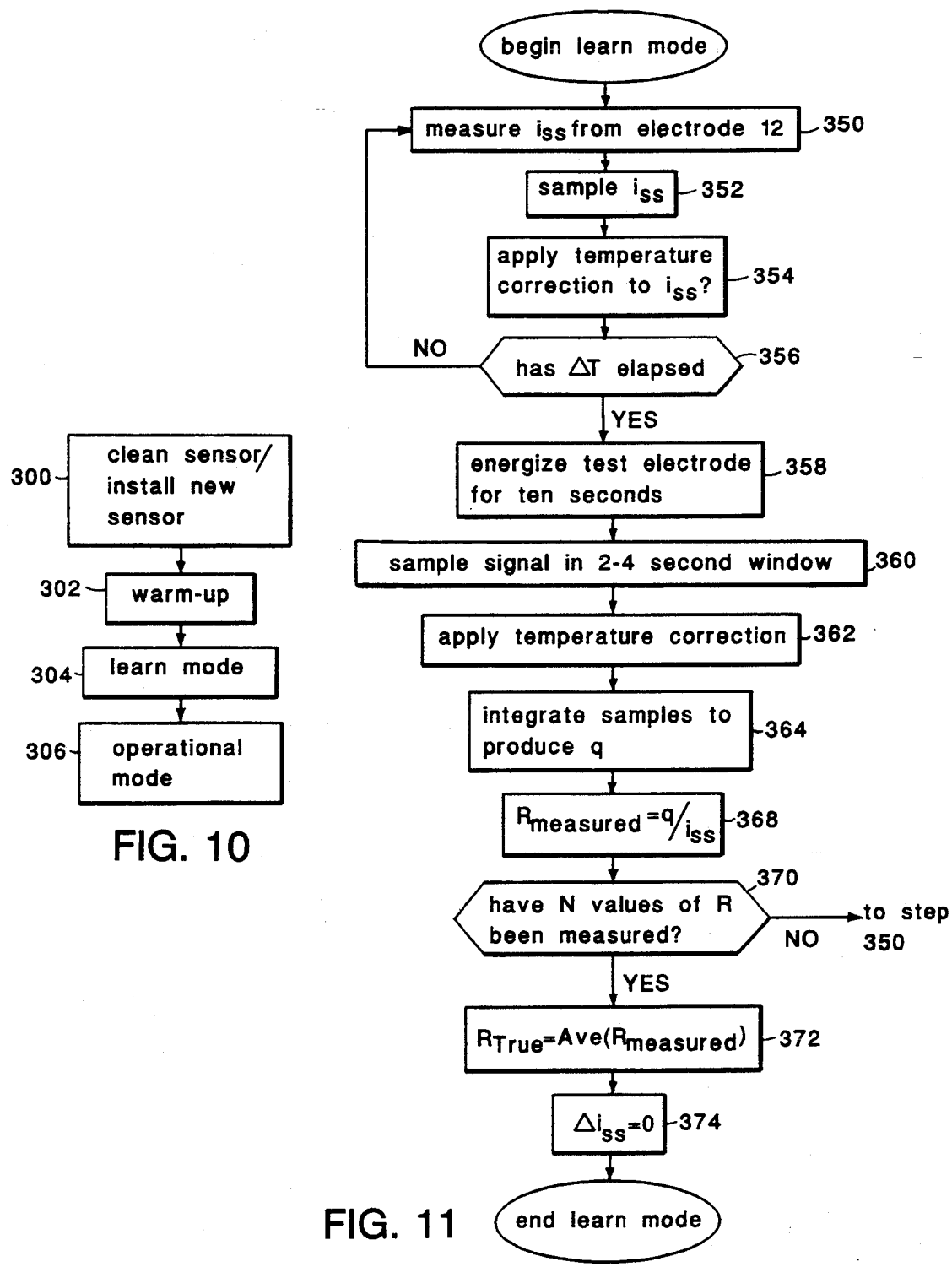

FOULING COMPENSATION IN AN OXYGEN ANALYZER

CROSS REFERENCE TO RELATED APPLICATIONS

This is a continuation-in-part of U.S. patent application No. 07/954,395 filed Sep. 30, 1992, now U.S. Pat. No. 5326447.

BACKGROUND OF THE INVENTION

This invention relates to analyzers for determining the level of a selected chemical in a process fluid.

A typical analyzer for measuring the level of a chemical in a process fluid includes a voltammetric sensor that supports one or more electrodes in electrolytic contact with the fluid. The electrodes are immersed in an electrolytic solution of fixed composition at one end of the sensor and are separated from the process fluid by a membrane that is permeable to the selected chemical. This type of sensor is known as a Clark cell when the chemical to be measured is oxygen or its allotropes such as ozone.

When the sensor is inserted in the process fluid and an oxygen-permeable membrane is used, oxygen in the fluid diffuses through the membrane into the electrolytic solution. As a result, when the electrodes are energized (with either D.C. or pulsed potential) they produce an electrical signal that is proportional to the level of oxygen in the electrolyte, and hence the amount of oxygen in the process fluid.

Such sensors may be adversely affected by membrane breakage or fouling. For example, the membrane may become fouled during use by materials (such as dirt, oil, grease, sludge, etc.) in the process fluid that collect on the membrane, reducing its permeability. As a result, the signal produced by the sensor will no longer accurately reflect the oxygen level in the process fluid, thereby leading to measurement errors. This problem is particularly acute when the process fluid comprises sludge-laden waste water in sewage treatment plants.

SUMMARY OF THE INVENTION

The invention features measuring the level of a chemical in a fluid using an electrode assembly separated from the fluid by a membrane. The level of chemical in the fluid is measured accurately and reliably, even when the membrane is fouled.

In one general aspect of the invention, the electrode assembly is energized to generate a steady state signal and a pulsed signal. The steady state signal and the pulsed signal both indicate a level of chemical in the fluid, but only the pulsed signal is substantially unaffected by fouling of the membrane. The pulsed signal and the steady state signal are used to determine a predicted value that the steady state signal will have in the absence of membrane fouling. The predicted value is used to correct the steady state signal to compensate for fouling of the membrane.

Preferred embodiments of the invention include the following features.

The electrode assembly includes a measurement electrode that produces the steady state signal, and a test electrode that produces the pulsed signal. The measurement electrode is continuously energized and the test electrode is periodically energized to produce two independent signals related to the level of chemical in the fluid. In particular, the measurement electrode is energized long enough for the steady state signal to reach its steady-state value, whereas the test electrode is energized for a shorter time that is insufficient to allow the pulsed signal to reach a steady-state value. The time intervals during which the test electrode and the measurement electrode are energized may be, but need not be, mutually exclusive.

The pulsed signals produced during test electrode energizations and the steady state signal produced by the measurement electrode are used to determine the predicted value. This predicted value is used to correct the steady state signal. In some embodiments, a correction factor is calculated from the predicted value each time the test electrode is energized, and the correction factor is used to correct the steady state signal after each completion of test electrode energization. Typically, the correction factor remains constant between test electrode energizations.

In some embodiments, the predicted value is calculated by measuring several successive pulsed signals and the steady state signal while the membrane is still unaffected by fouling, typically during calibration. The pulsed signals are integrated over a fixed time interval, and a calibration ratio of each integrated pulsed signal to the steady state signal is determined. These calibration ratios are then averaged to provide an accurate measure of the electrode assembly and membrane characteristics. During fouling compensation, several pulsed signals are measured, integrated, and averaged. The predicted value used to correct the steady state current is determined by causing a ratio of the averaged pulsed signals to the predicted value to be equal to the averaged calibration ratio.

When calculating the predicted value, the pulsed signals are each integrated over the same time window during energization of the test electrode. This time window is always shorter than the duration of the pulsed signal. In other embodiments, only one pulsed signal is used to find the calibration ratio, and only one pulsed signal is used to correct the steady state signal.

After the predicted value has been calculated, it is compared to the steady state signal to produce a correction factor for the steady state signal. Typically, the difference between the predicted value and the steady state signal provides the correction factor. Alternatively, the steady state signal may be corrected by substituting the predicted value for the steady state signal.

The corrected steady state signal is substantially free of fouling effects, and is used to accurately determine the level of the chemical in the fluid. In some embodiments, a measurement of the steady state signal is corrected only if the level of chemical in the fluid exceeds a given threshold.

In addition, an alarm is activated upon determining that the membrane has been fouled to a given extent. For example, the alarm may be activated when the difference between the predicted value and the steady state signal exceeds a given threshold. Alternatively, the alarm is activated when a ratio between the integrated pulsed signal and the steady state signal exceeds the averaged calibration ratio by a given amount.

Advantages of the invention include the following.

By compensating for fouling of the membrane in a straightforward manner, the invention allows the level of chemical in the fluid to be measured accurately and reliably, even as the membrane becomes fouled, or as the level of fouling increases. As a result, the membrane may be used while the membrane becomes fouled during normal use, and in fact the membrane may be used even when fouled to a significant degree. This significantly extends the useful life of the sensor.

The invention compensates for fouling in real time, without interfering in any significant way with the measurement of the level of chemical in the fluid. Because the test electrode is energized for only brief periods between relatively long time intervals, and the measurement electrode is continually energized, the fouling compensation is essentially transparent to the steady-state measurement of chemical level provided by the measurement electrode.

In addition, by calculating a calibration ratio, the fouling compensation scheme described above is compatible with any type of voltammetric sensor having a permeable membrane. For example, the fouling compensation scheme can be used with sensors having electrodes with different areas, membranes with varying thicknesses, and membranes constructed of different materials. The sensor may thus be modified or replaced, without requiring any change in the fouling compensation scheme.

Other features and advantages of the invention will become apparent from the following detailed description, and from the claims.

BRIEF DESCRIPTION OF THE DRAWINGS

FIG. 10 is a flowchart of the operation of an analyzer performing fouling compensation.

FIG. 11 is a flowchart of the "learn mode" step shown in FIG. 10.

DESCRIPTION OF THE PREFERRED EMBODIMENTS

Figure 1:
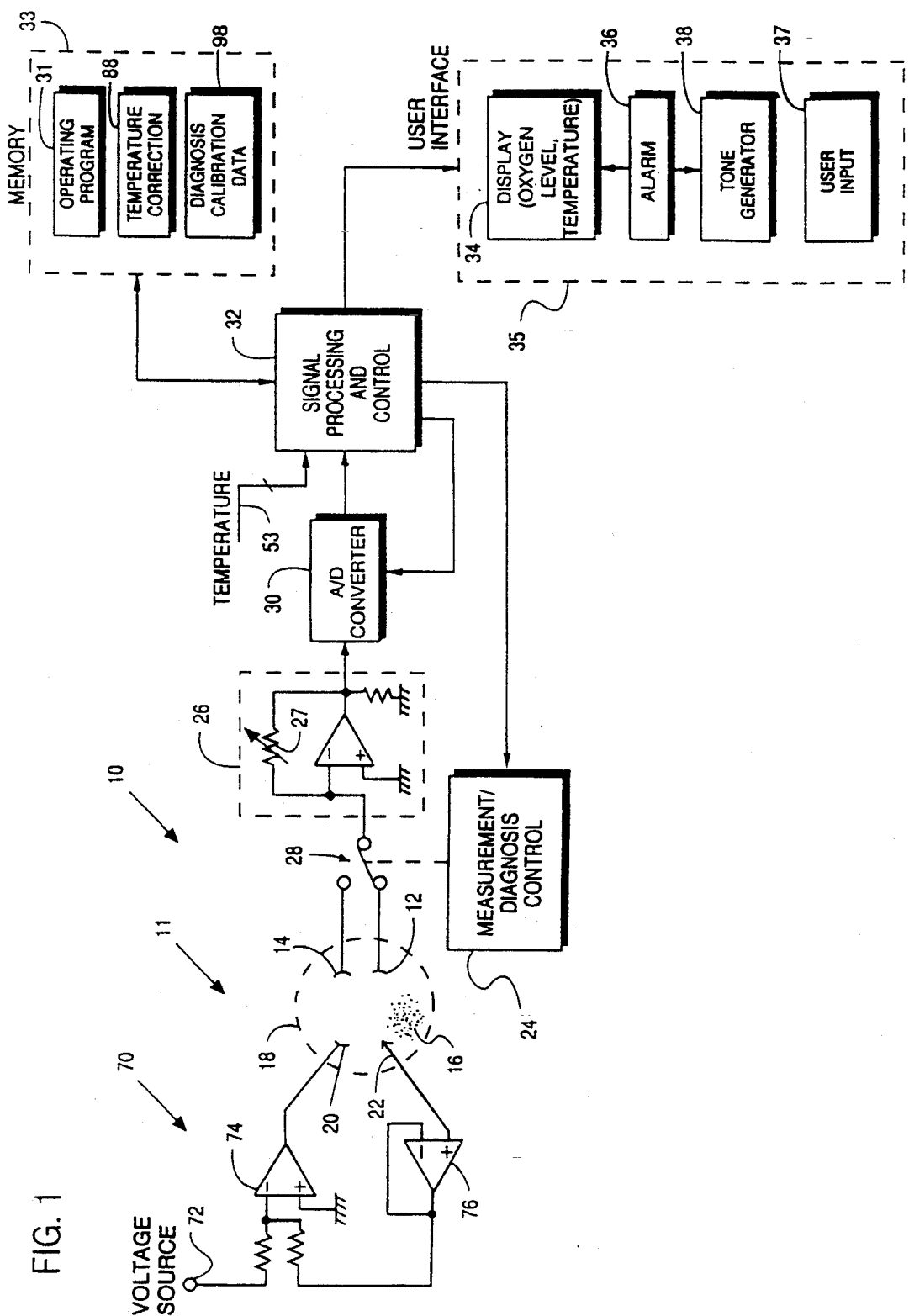
FIG. 1 is a functional block diagram of a chemical analyzer according to the invention, which includes a sensor for measuring the level of oxygen in a process fluid.

Referring to FIG. 1, an analyzer 10 for measuring the level of a selected chemical in a process fluid (not shown) includes a sensor 11 that contains a measurement electrode 12 and an adjacently disposed test electrode 14 immersed within an electrolyte solution 16 (only a portion of which is depicted) and enclosed by a membrane 18. Membrane 18 is permeable to the selected chemical, which is, for example, oxygen or its allotropes. Also enclosed by membrane 18 are an auxiliary electrode 20 for supplying energizing current to electrodes 12, 14, and a reference electrode 22 for allowing the voltage at electrodes 12, 14 to be maintained relatively constant for purposes to be described. Each electrode 12, 14 when energized produces an electrical current the amplitude of which is proportional to the level of oxygen that has diffused into the electrolyte solution from the process fluid.

Electrodes 12, 14 are selectively energized by measurement/diagnosis controller 24 at mutually exclusive times and for different durations. Controller 24 performs this function by selectively coupling electrodes 12, 14 to a current-to-voltage converter 26 (switch 28 schematically represents this function), which completes the electrical circuit with auxiliary electrode 20 and transforms the current produced by the selected electrode to a voltage that represents the level of oxygen in the process fluid. A variable resistor 27 in converter 26 allows the user to set the gain of the current to voltage conversion.

The voltage is digitized by an analog-to-digital (A/D) converter 30 and analyzed by a processor 32, which also controls the operation of controller 24 and A/D converter 30. Processor 32 operates under the control of a program 31 stored in memory 33. It will be appreciated that the functions of at least controller 24 and processor 32 can be implemented by a microprocessor; separate units are shown for ease of explanation.

The operation of analyzer 10 is discussed in detail below. Suffice it here to say that measurement electrode 12 is energized in a manner selected so that electrode 12 produces a signal representative of the oxygen level in the process fluid, and test electrode 14 is periodically energized in place of measurement electrode 12 to develop a signal used by processor 32 in conjunction with the previously obtained signal from measurement electrode 12 to determine whether membrane 18 has become faulty (e.g. fouled or coated with material such as dirt, sludge, waste, oil, grease, etc.).

More specifically, measurement electrode 12 is energized for a time period sufficient to allow the current response thereof to reach a steady-state level. For example, electrode 12 is energized for between 15 minutes and 1 hour or more. As a result, in the absence of a fault in membrane 18 the current produced by electrode 12 (and hence the voltage applied to processor 32) is linearly related to the rate at which oxygen diffuses from the process fluid to electrolyte 16 across membrane 18, and thus the current is proportional to the oxygen level in the fluid. Processor 32 displays the measured oxygen level to the user (e.g., as a concentration in parts per million (ppm) or as a percent saturation) by illuminating a display 34 on user interface 35 (which is located, e.g., on the front panel of a housing that contains the circuitry discussed above). Alternatively, the measured oxygen level may be sent to a process control computer for adjusting the oxygen level in the process fluid, to a data logger, or to a printer (none of these devices are shown).

If membrane 18 becomes faulty (for example, if membrane 18 becomes fouled with a coating of material that interferes with oxygen permeability), the rate of oxygen diffusion across membrane 18 slows, thereby decreasing the steady-state signal produced by measurement electrode 12 so that it no longer accurately represents the oxygen level of the process fluid. To enable analyzer 10 to diagnose membrane fouling, processor 32 periodically commands controller 24 to briefly energize test electrode 14 (by inserting test electrode 14 into the circuit of auxiliary electrode 20 in place of measurement electrode 12). Test electrode 14 is energized sufficiently briefly (e.g., on the order of 10 seconds) so that its current response does not reach a steady-state level. As a result, the oxygen level measured by test electrode 14 is the equilibrium level of the oxygen established in electrolyte 16 during the time that measurement electrode 12 was energized, rather than the rate of oxygen diffusion across membrane 18. Thus, any fouling of membrane 18 does not appreciably degrade the current level produced by electrode 14. Accordingly, processor 32 determines whether membrane 18 has become fouled by comparing the signal produced by test electrode 14 with the oxygen level as measured with electrode 12 in a manner described in detail below.

If the signal produced by test electrode 14 indicates that the process fluid contains an appreciably greater level of oxygen than that indicated by the steady-state current level produced by measurement electrode 12, processor 32 determines that membrane 18 has become fouled and alerts the user by generating an alarm 36. Alarm 36 may be visual (for example, processor 32 may alter the oxygen level display 34 from a continuous to a blinking signal). In addition (or alternatively), alarm 36 may be audible, such as a tone 38. The user can respond to the alarm by either cleaning membrane 18 or replacing it with a new membrane.

Figure 2:
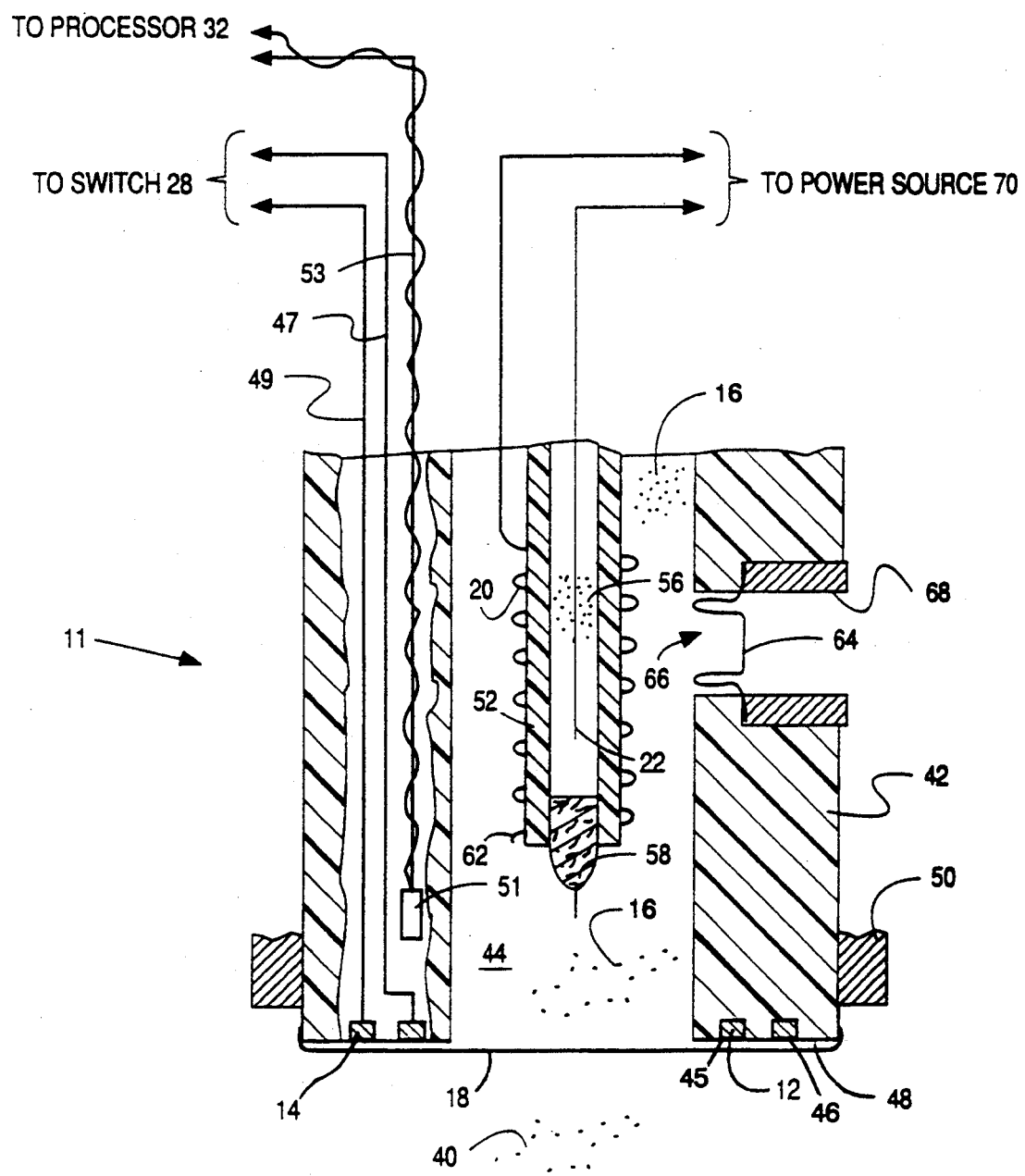
FIG. 2 is a partial cross-sectional view of a portion of the sensor of the chemical analyzer of FIG. 1.
Figure 3:
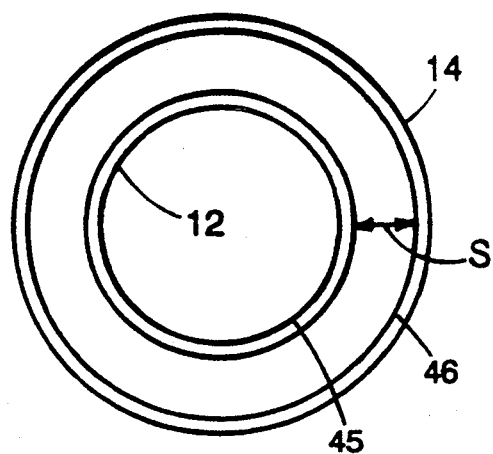
FIG. 3 is an end view of the sensor of FIG. 2 that shows the arrangement of two of the electrodes of the sensor.

Referring to FIGS. 2 and 3, the end of sensor 11 that is constructed to be inserted into process fluid 40 is shown in detail. Sensor 11 includes a hollow housing 42 made from Kynar®, a plastic PVDF (poly vinylidene difluoride) commercially available from the Penwalt Corporation. The distal end of housing 42 supports a pair of coaxial gold or platinum rings that comprise measurement electrode 12 and test electrode 14, respectively. Measurement electrode 12, is disposed radially inwardly of test electrode 14, but the positions of electrodes 12, 14 may of course be reversed. An interior chamber 44 of housing is filled with electrolyte solution 16 which is, for example, a 2 molar KCl (potassium chloride) that supports the electrochemical reaction of oxygen at electrodes 12, 14. Solution 16 may also include a surfactant and an algicide.

Membrane 18 is stretched tightly over the face 48 of housing 42 in which electrodes 12, 14 are embedded and is secured in place by a collar 50 that is attached to housing 42 with threads (not shown). Membrane 18 is thin (e.g., between 0.5 mils and 5 mils thick) and is made from any suitable material that is highly permeable to oxygen. For example, membrane 18 is Teflon®, silicone rubber, or polyethylene. The spacing between membrane 18 and electrodes 12, 14, is quite narrow (and is shown greatly exaggerated for purposes of illustration) but is sufficient to allow a thin film of electrolyte solution 16 to form therebetween by capillary action.

A spacing S (e.g., 1/8 inch) separates measurement electrode 12 and test electrode 14 so that electrodes 12, 14 are exposed to different annular regions 45, 46 of a the film of electrolyte solution 16. When measurement electrode 12 is energized, oxygen that permeates membrane 18 into the film of electrolyte 16 in region 45 is electrochemically consumed as the oxygen reaches measurement electrode 12. Because test electrode 14 is de-energized during this time, oxygen that diffuses through membrane 18 into annular region 46 of electrolyte 16 is not consumed. Thus, the oxygen in region 46 is in equilibrium with the concentration of oxygen in process fluid 40. It is this level of oxygen that is measured when test electrode 14 is briefly energized to diagnose membrane fouling. The seal between membrane 18 and housing 42 and the energization of measurement electrode 12 serve to avoid lateral diffusion of oxygen to test electrode 14 from fluid 40 and the electrolyte in cavity 44, respectively.

The walls of housing 42 are hollow to accommodate wires 47, 49 that provide the electrical connections between switch 28 (FIG. 1) electrodes 12, 14, respectively. In addition, a thermistor 51 is suspended near the distal end of housing 42 by a pair of wires 53. Processor 32 (FIG. 1) uses the temperature measurement of electrolyte 16 provided by thermistor 51 (which indicates the temperature of fluid 40) to apply temperature correction to the oxygen level measurement, as described below.

A tube 52 is suspended within chamber 44 and supports reference electrode 22 (FIG. 1), which is a silver wire coated with silver chloride immersed in an electrolyte solution 56 of KCl. A porous ceramic wick 58 mounted in the distal end of tube 52 maintains electrolytic contact between solutions 16 and 56, and limits the internal diffusion of KCl between chamber 44 and the interior of tube 52. As explained below, this allows reference electrode 22 to be used to control the potential at electrodes 12, 14 when electrodes 12, 14 are energized.

Auxiliary electrode 20 (FIG. 1) is a silver wire in the form of a coil that is wrapped around tube 52 (only a portion of each winding is shown for clarity). The end 62 of the silver wire that forms auxiliary electrode 20 is disposed adjacent to the distal end of tube 52. Silver is used to avoid adding oxygen to electrolyte 16 (which would occur if material such as platinum or gold were to be used for electrode 20 and would disrupt the measurement) when auxiliary electrode 20 oxidizes during operation.

A pressure relief diaphragm 64 is held over a side opening 66 in chamber 44 by a plug 68. Diaphragm 64 is held at a much lower tension than membrane 18 so that diaphragm 64 expands and contracts preferentially to membrane 18 in response to changes in the pressure of electrolyte 16. For example, a gaseous bubble (not shown) trapped in chamber 44 will cause diaphragm 64 rather than membrane 18 to expand in response to temperature changes or pressure (depth of immersion) variations experienced by sensor 11. This helps maintain a constant spacing between membrane 18 and electrodes 12, 14 despite pressure changes in electrolyte 16. Because the rate of oxygen diffusion of from process fluid 40 to electrodes 12, 14 is a function of the spacing of membrane 18, a nonvariable spacing is critical to the accuracy of the oxygen level measurement.

Referring also to FIG. 1, auxiliary electrode 20 and reference electrode 22 are connected to a power source 70 that controls the level of current applied to the energized electrodes 12, 14. Energizing current for electrodes 12, 14 is provided by a D.C. voltage source 72 via a current driver 74. The polarity of the voltage applied by source 72 is selected to polarize electrodes 12, 14 in the cathodic direction. The current response of electrodes 12, 14 is linear with respect to the oxygen level in process fluid 40 when electrodes 12, 14 are energized at a potential of between about $-0.6$ volts and $-1.5$ volts with respect to reference electrode 22. Reference electrode 22 provides (through a high impedance voltage follower 76) negative feedback for driver 74 to maintain each electrode 12, 14 squarely within its linear range when energized (e.g., at a potential of −0.7 volts with respect to reference electrode 22).

Figure 4:
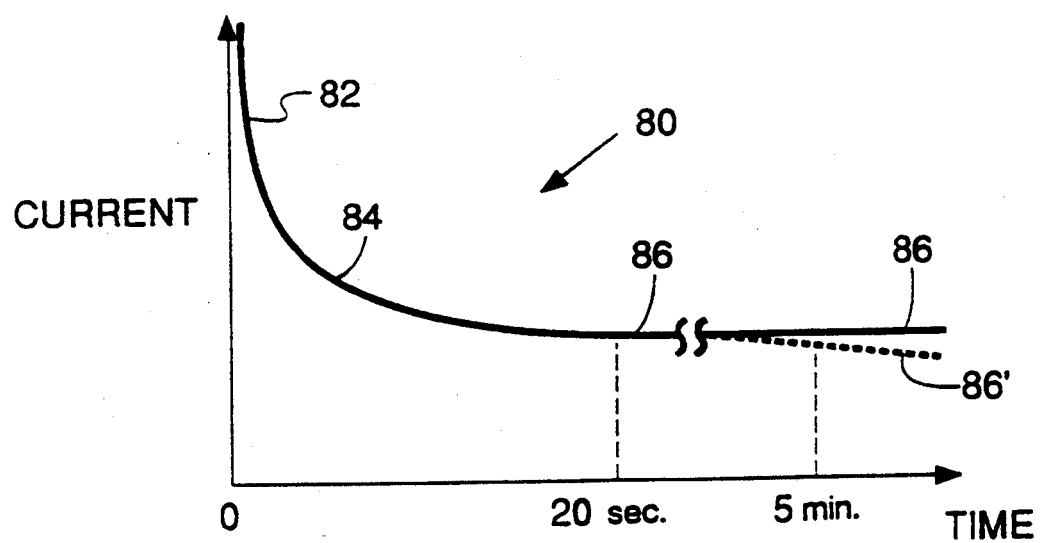
FIG. 4 illustrates the current-time response of one of the electrodes of the sensor of FIGS. 1 and 2.

Referring to FIG. 4, in operation, processor 32 begins the measurement process at time t=0 by commanding controller 24 to connect measurement electrode 12 to current to voltage converter 26 through switch 28, thereby completing the circuit with auxiliary electrode 20 and energizing measurement electrode 12. The oxygen concentration at the surface of electrode 12 is immediately driven to zero as the O₂ at the surface of electrode 12 is faradaically reduced to OH⁻ according to the following equation:

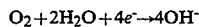

$$O_2 + 2H_2O + 4e^- \rightarrow 4OH^-$$

As a result, immediately after time 0, measurement electrode 12 produces a high level of current that decays to a steadystate level according to curve 80. As shown by region 82 of curve 80, the current is initially capacitive (due to the charging of the double-charge layer at the surface of measurement electrode 12) as well as faradaic (due to the reduction of oxygen present at the surface of electrode 12). The immediate exhaustion of oxygen at the surface of electrode 12 causes oxygen to begin diffusing from process fluid 40 to electrolyte 16 across membrane 18, thereby slowing the rate of current decay. The current level continues to fall (as shown in region 84 of curve 80) and ultimately reaches a steady-state value that is proportional to the oxygen concentration gradient established across membrane 18 in region 45 of electrolyte 16.

The current reaches its steady-state value approximately 20 seconds after electrode 12 is energized. At this time, the rate at which electrode 12 reduces oxygen to OH⁻ becomes fixed by the rate of oxygen diffusion across membrane 18 and is linearly proportional to the amount of oxygen in process fluid 40. Thereafter, in the absence of a fault (such as fouling of membrane 18) or a change in the oxygen level of fluid 40, the current level produced by electrode 12 will remain constant, as shown by region 86 of curve 80.

Processor 32 measures the steady-state current produced by electrode 12. As a result, processor 32 waits for about 1 minute after time 0 before beginning to analyze the signals from electrode 12. The analog current produced by measurement electrode 12 is converted to a voltage by current to voltage converter 26, and this voltage is repeatedly sampled and digitized by A/D converter 30. Processor 32 controls A/D converter 30 to sample the analog voltage every 33 milliseconds, but of course other sampling periods may be employed.

Processor 32 converts the values (i.e., the amplitudes) of the digital samples to derive the oxygen concentration (in parts per million, ppm) of fluid 40 by applying a constant of proportionality to the values. (The relationship between current and oxygen concentration is described in *Measurement of Dissolved Oxygen*, by Michael L. Hitchman, John Wiley & Sons, 1978.) Because the temperature of sample 40 affects the current produced by electrode 12, processor applies a temperature correction factor (stored in a table 88 in memory 33) to the derived oxygen concentration based on the temperature measured by thermistor 51. (The circuitry for digitizing the thermistor signal is not shown.) The temperature-compensated oxygen level can then be displayed 34 as a concentration of oxygen in ppm, or alternatively processor 32 may convert the oxygen level to another unit of measurement (such as percent saturation) and display the same. Periodically, or upon user command from an input 37 (such as a keypad on the front panel), processor 32 sends the temperature measurement to display 34 in place of the oxygen level.

Because the steady-state current 86 produced by measurement electrode 12 is a function of the rate at which oxygen diffuses across membrane 18, steady-state current 86 will decrease if the diffusion of oxygen is hampered. For example, oxygen-impermeable material (e.g., dirt, algae, oil, etc.) in process fluid 40 that collect on membrane 18 interfere with the diffusion of oxygen, thereby "fouling" membrane 18 and decreasing the current produced by electrode 12 so that the current no longer accurately reflects the oxygen concentration in fluid 40. This is shown by dashed portion 86′ of current curve 80 in FIG. 4. The problem of fouling is particularly acute in applications in which sensor 10 is used with highly contaminated process fluids 40 (such as waste water in sewage treatment plants).

Figure 5:
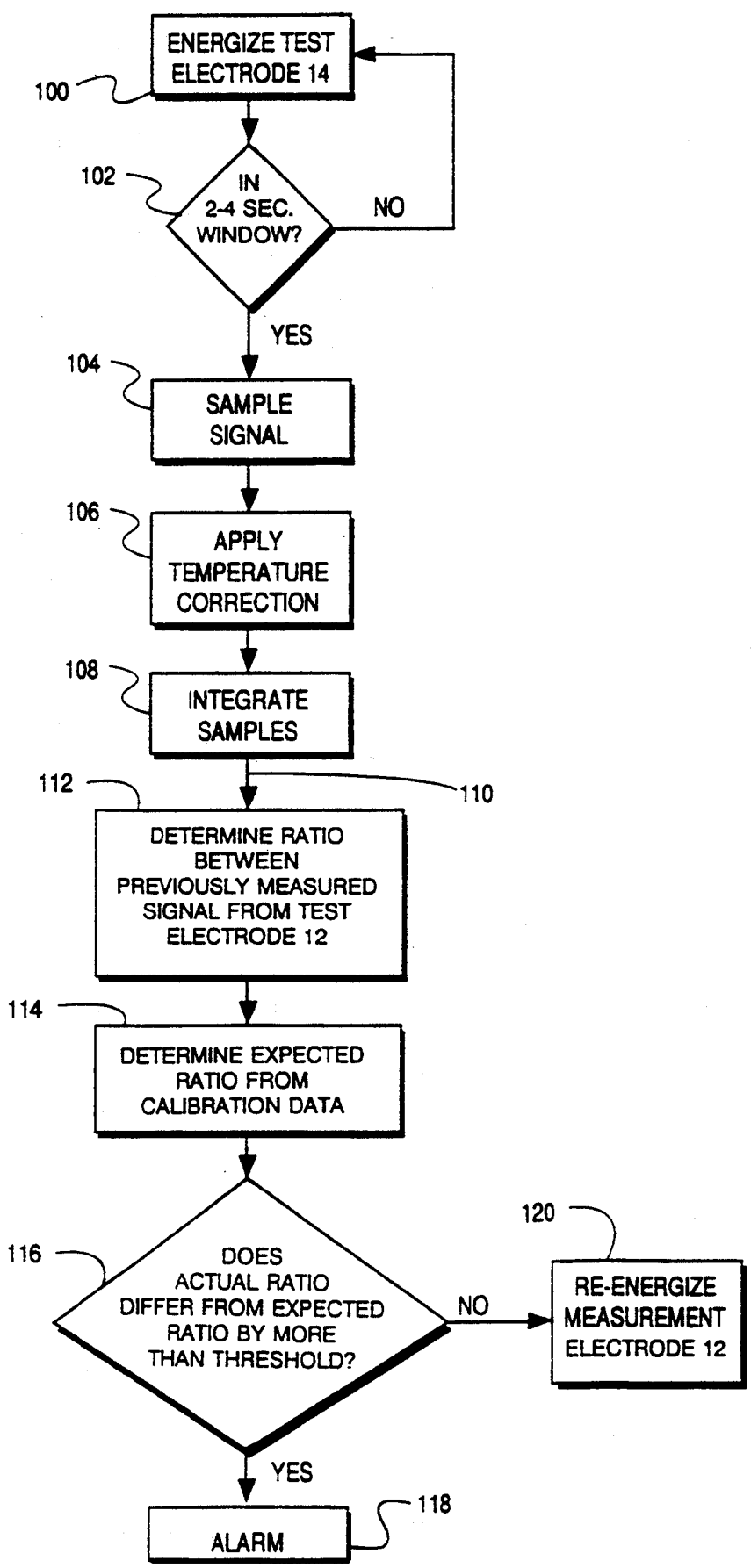
FIG. 5 is a flow chart useful in understanding how the analyzer of FIG. 1. diagnoses membrane fouling.

Referring also to FIG. 5, processor 32 periodically commands controller 24 to briefly energize test electrode 14 via switch 28 in place of measurement electrode 12 (step 100) and analyzes the resulting signal produced by test electrode 14 to determine whether membrane 18 has become fouled. The user can adjust the intervals between successive energizations (e.g., 15 minutes to 1 hour or more) as well as the duration of time that test electrode 14 is energized via input 37. The duration that test electrode 14 is energized should be insufficient for the current response of test electrode 14 to reach a steady-state level, and should also be sufficiently brief that measurement electrode 12 does not become discharged before it is reenergized by controller 24 (thereby allowing measurement electrode 12 to rapidly return to its steady state response when it is re-energized). Energizing test electrode 14 for 10 seconds between successive energizations of measurement electrode 12 has been found to be satisfactory for these purposes.

Figure 6:
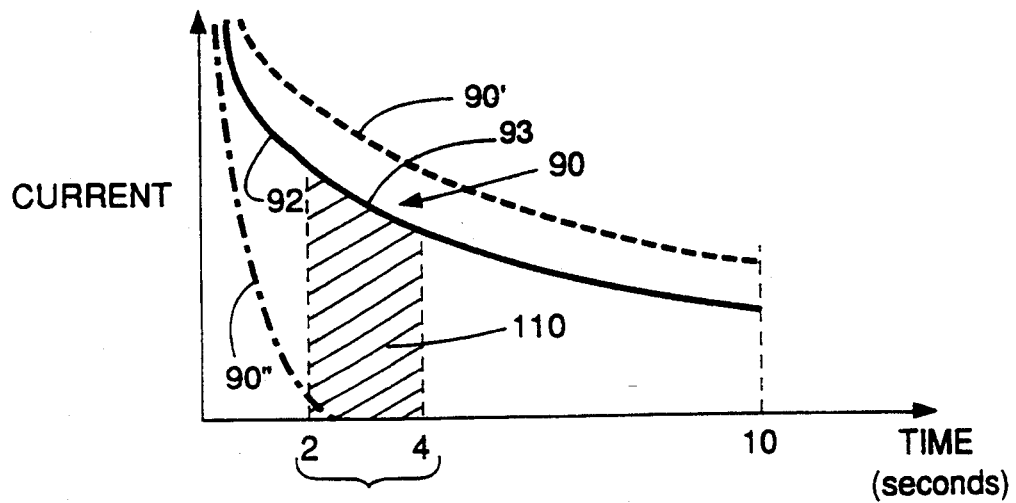
FIG. 6 illustrates the current-time response of another electrode of the sensor of FIGS. 1 and 2.

Referring also to FIG. 6, curve 90 illustrates the current response of test electrode 14. Because of the spacing between electrodes 12, 14, the oxygen concentration gradient established in region 45 of electrolyte by the steady-state operation of measurement electrode 12 does not deplete the level of oxygen in region 46 of electrolyte 16 disposed between test electrode 14 and membrane 18. Thus, immediately prior to the time that test electrode 14 is energized, the oxygen level in electrolyte region 46 is at equilibrium with the level of oxygen in fluid 40.

As explained above, immediately after test electrode 14 is energized, the oxygen at the surface of test electrode 14 is depleted, causing electrode 14 to produce a high level of current that decreases toward a steady state level as oxygen diffuses across membrane 18. For the first second or so after test electrode 14 is energized (region 92 of curve 90), the current has a large capacitive component and is ignored by processor 32. After this interval and before the steady-state current level is reached, the amount of current produced by test electrode 12 is a function of the rate at which the oxygen is exhausted in region 46 of electrolyte between test electrode 14 and membrane 18, as shown by region 93 of curve 90. Curve 90 represents approximately a 50% oxygen saturated sample. (For comparison, curve 90′ shows the current response for a 100% oxygen saturated sample 40, while a sample 40 that contains no oxygen results in a current response shown by curve 90".)

Processor 32 analyzes the current produced by test electrode 14 during a portion of the time period that electrode 14 is energized, for example, during time window 94 of between 2 seconds and 4 seconds of the 10 second duration that electrode 14 is energized (step 102). During time window 94, A/D converter 30 provides processor 32 with about 60 samples (step 104) (at the 33 millisecond sampling rate) of the voltage produced by converter 26 in response to the current from test electrode 14. Processor 32 applies temperature correction (step 106) to the values of the samples (using stored table 88) and then integrates (step 108) the samples by adding them together and dividing the sum by the number of samples. The result corresponds to the total charge (in Coulombs) 110 gathered by test electrode 14 during the 2-4 second time window.

Due to the relatively brief interval that test electrode 14 is energized, the current produced by test electrode 14 does not reach a steady-state level and thus is not affected by the rate at which oxygen diffuses through membrane 18 into electrolyte region 46. As a result, applicant has found that total charge 110 is substantially independent of the degree of fouling of membrane 18. That is, for a given oxygen concentration of process fluid 40, total charge 110 will be substantially the same independently of whether membrane 18 is completely clean or is fouled. Thus, by comparing total charge 110 with the previously obtained steady state oxygen level measurement from measurement electrode 12 in the manner described below, processor 32 determines whether membrane 18 has become fouled and, if so, notifies the user by activating alarm 38.

Total charge 110 will rarely, if ever, equal the previously obtained steady state oxygen level measurement and in fact should exceed it. Applicant has found that the difference between total charge 110 and the steady state oxygen level measurement increases as membrane 18 becomes fouled. The reason is that fouling causes the steady-state current produced by measurement electrode 12 to decrease (as shown by curve 86' in FIG. 5) but does not cause a similar reduction in total charge 110, as discussed above. Thus, processor 32 determines the ratio between total charge 110 and the previously-obtained steady-state measurement of the oxygen level (step 112), and compares the actual ratio with the ratio that would be expected for a non-fouled electrode (steps 114, 116). If the actual ratio differs from the expected ratio by more than a threshold amount, processor 32 determines that membrane 18 has become fouled.

Figure 7:
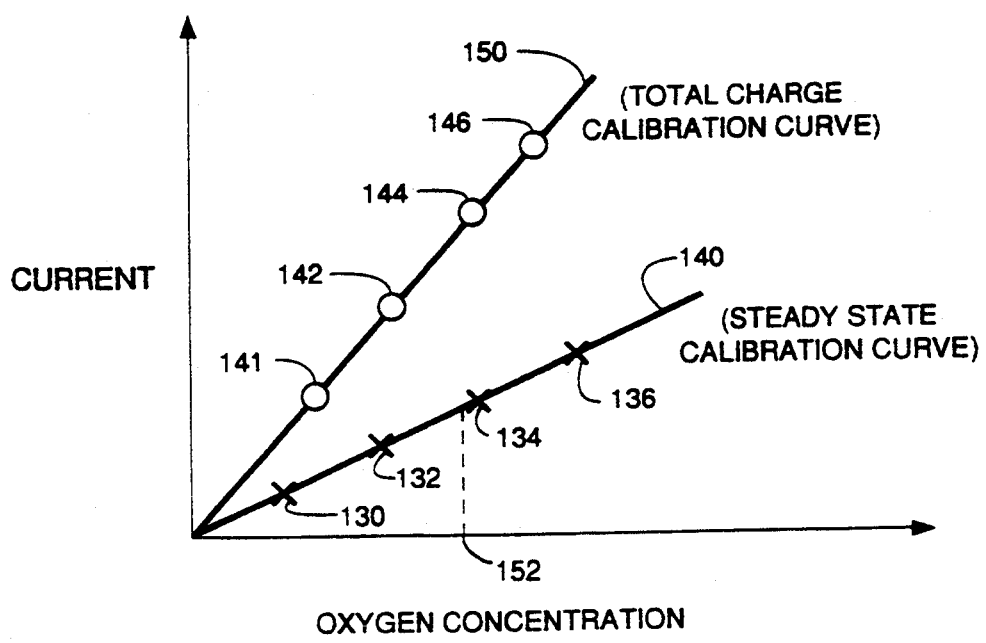
FIG. 7 shows a calibration chart useful in understanding how membrane fouling is diagnosed.

Referring to FIG. 7, processor 32 determines the expected ratios between total charge 110 and the steady state oxygen level measurements as a result of calibration of analyzer 10 with a clean membrane 18. During calibration, analyzer 10 makes a series of (e.g., four) steady-state measurements 130, 132, 134, 136 of the oxygen concentration of process fluid 40 using measurement electrode 12 in the manner described above. Each steady state measurement is made by energizing electrode 12 for 15 minutes. At the end of each 15 minute period, processor 32 stores the digitized, temperature corrected current from measurement electrode 12 in a working area 98 of memory 33 (FIG. 1). Steady state measurements 130-136 define a curve 140 that is linear with respect to the oxygen concentration of process fluid 40.

During calibration, analyzer 10 also performs a series of (e.g., 4) total charge measurements 141, 142, 144, 146 in the manner discussed above using test electrode 14. Total charge measurements 141-146 define a linear curve 150 with respect to oxygen concentration and are stored in working memory area 98. For any given concentration of oxygen in fluid 40 (such as concentration 152) the ratio between the total charge value on curve 150 and the steady state value on curve 140 defines the expected ratio used by processor 32 in step 116 (FIG. 5).

Thus, during operation, after processor 32 determines (step 112) the actual ratio between total charge 110 and the previously measured oxygen concentration, processor 32 determines (step 114) the expected ratio for the previously measured oxygen concentration using the calibration data stored in working memory area 98. The linearity of curves 140, 150 with respect to oxygen concentration makes this a relatively straightforward calculation. If the expected ratio exceeds the actual ratio by a threshold of, e.g., 30%, processor 32 determines that membrane 18 has become fouled and activates the alarm (step 118). Otherwise, processor commands controller 24 to reenergize electrode 12 (step 120) to begin the next measurement period.

The 30% threshold can be made stricter (e.g., reduced to 10% or less) or larger (e.g., increased to 50% or more), depending upon the tolerance to fouling that the user desires. Requiring a closer match between the expected and actual ratios will obviously alert the user when only a small amount of fouling has occurred. This may be advantageous in applications in which inaccuracies caused by even minor fouling are not desirable. In other, less stringent applications, the threshold may be increased so that the user is alerted only when membrane 18 is severely fouled.

Other embodiments are within the scope of the following claims.

For example, analyzer 10 can be used to measure the levels of chemicals other than oxygen by selecting suitable electrolyte and electrode materials. Fouling diagnoses can be based on the differences between the expected values on curves 140, 150, rather than their ratios.

Electrodes 12, 14 need not be energized for mutually exclusive time intervals.

Processor 32 can alternatively use the fouling determination to correct the oxygen level measurement. Analyzer 10 can also perform other fault diagnoses.

Figure 8:
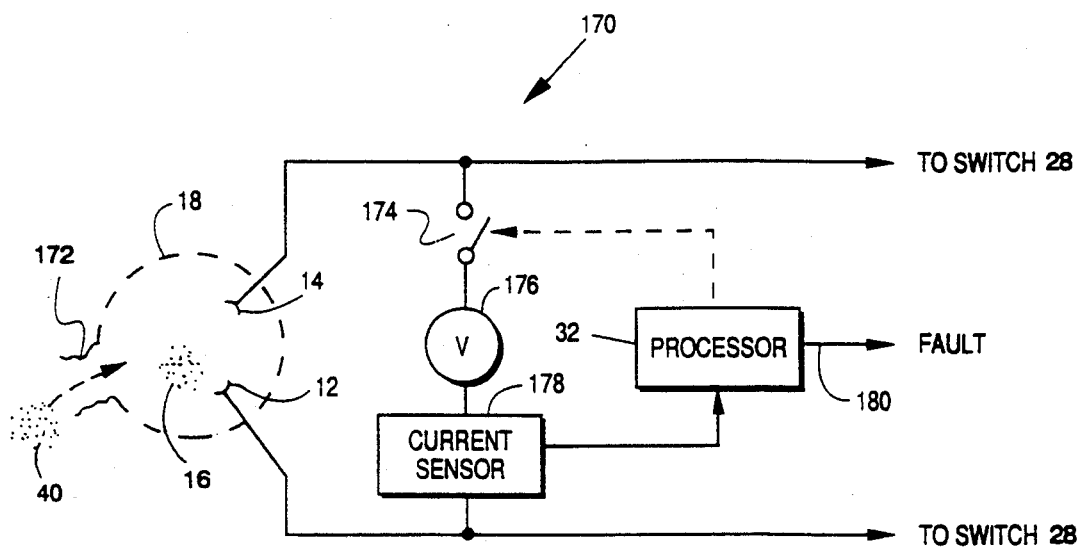
FIG. 8 is a functional block diagram of circuitry for detecting a rupture in the membrane of the sensor of FIGS. 1 and 2.

For example, referring to FIG. 8, circuitry 170 enables processor 32 to detect a rupture 172 in membrane 18 by detecting changes in the electrical resistance between electrodes 12, 14. The resistance presented by electrolyte 16 (e.g., 2 molar KCl) is approximately 300 ohms. A rupture 172 in membrane 18 would permit some of process fluid 40 (which is, e.g., waste water) to mix with electrolyte 16, thereby altering the resistance between electrodes 12, 14.

After each time window 94 (FIG. 6) but while test electrode 14 is energized, processor 32 closes a switch 174 to apply an A.C. voltage from a source 176 across electrodes 12, 14. The voltage produced by source 176 is at a relatively high frequency (1000 Hz) and is small (100mV) so as not to interfere with the current response of either electrode. The resulting current between electrodes 12, 14 is measured by sensor 178, and the measurement is digitized (not shown) and applied to processor 32. Processor 32 applies temperature correction to the current level according to the temperature measured by thermistor 51. (Temperature correction may be omitted, if desired.) If the resistance indicated by the current differs from 300 ohms by more than a threshold amount (e.g., is outside of the range of 100 ohms to 1000 ohms), processor 32 generates a fault 180, which is displayed as an error message on display 34 (FIG. 1).

Because the resistance measurement is made after the current from test electrode 14 has been collected during time window 94, it does not interfere with the fouling diagnosis. Moreover, processor 32 opens switch 174 as soon as the resistance measurement has been completed (which takes one second or less). Thus, circuitry 170 is disconnected before measurement electrode 12 is reenergized.

Figure 9:
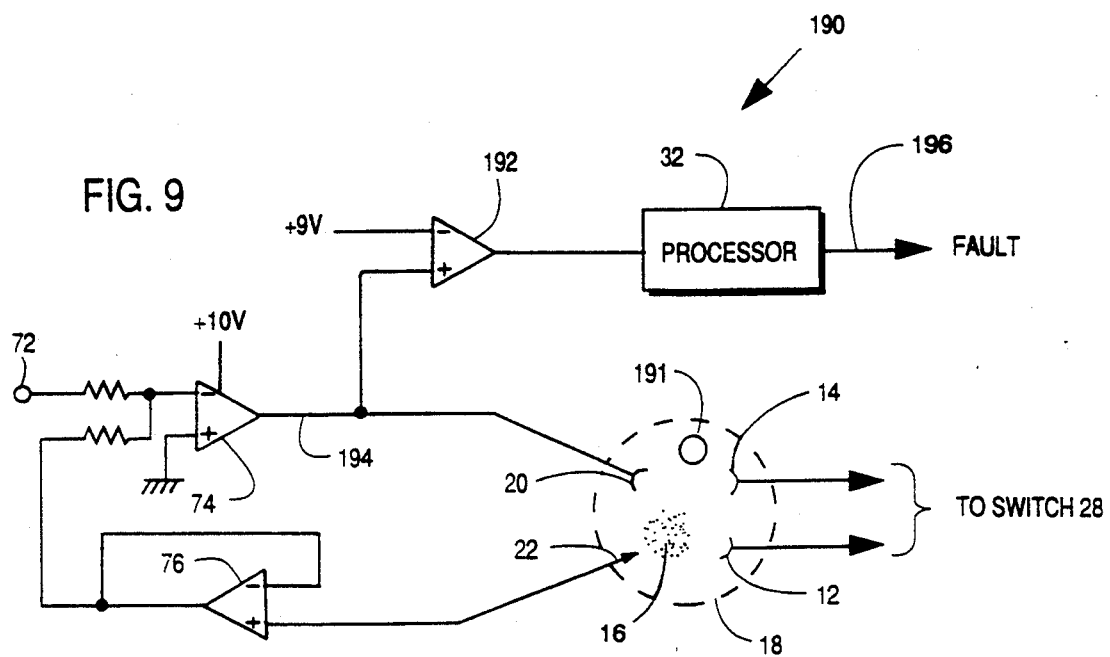
FIG. 9 is a functional block diagram of circuitry for detecting the presence of a gaseous bubble in the sensor of FIGS. 1 and 2.

Referring to FIG. 9, circuitry 190 detects loss of electrolytic solution 16 or the presence of one or more gaseous bubbles 191 in electrolyte 16. Although, as discussed above, pressure compensation diaphragm 64 (FIG. 2) helps maintain a fixed spacing between electrodes 12, 14 and membrane 18, the loss of electrolyte 16 or the presence of bubbles 191 in electrolytic solution 16 has other harmful effects. For example, loss of electrolyte 16 or the addition of gaseous bubbles increase the electrical resistance of the electrical path between auxiliary electrode 20 and measurement electrode 12 (or test electrode 14) through electrolyte 16, thereby requiring the output voltage produced by current driver 74 to increase to maintain each electrode 12, 14 when energized at the desired potential of −0.7 volts with respect to reference electrode 22. Of course, driver 74 cannot produce an output voltage that exceeds its supply voltage (e.g., +10 volts). When this maximum level is reached, driver 74 will be unable to compensate for further increases in the resistance of electrolyte 16. If this occurs, the potential on energized electrodes 12, 14 will fall, leading to errors in the oxygen measurement or fouling diagnosis.

Comparator 192 monitors the output voltage 194 of driver 74. If output voltage 194 exceeds a predetermined percentage (e.g., 90%) of the supply voltage (in this example, +9 volts), comparator 192 notifies processor 32. Processor 32 responds to this error by generating a fault 196, which is displayed as an error message on display 34.

An example of how the fouling determination can be used to correct the oxygen level measurement is shown in FIGS. 10 through 13, and is discussed in detail below.

The error correction procedure is summarized as follows. Referring to FIGS. 1 and 6, processor 32 performs the error calculation by first calibrating analyzer 10. This is done by measuring a calibration steady state current $i_{ss}$ and a calibration charge q (found by integrating the test electrode current within time window 94) when the membrane is not fouled. Processor 32 then determines the ratio $R_{true}$ of the calibration charge q to the calibration steady state current $i_{ss}$. This ratio is generally constant with respect to oxygen concentration in solution 16 for a clean membrane 18, but the ratio may vary for sensors 11 having different electrode areas, membrane thicknesses, or membrane materials.

As discussed above, fouling of membrane 18 will leave the value of q unchanged, but will cause the value of $i_{ss}$ (for a given oxygen concentration) to decrease with increasing fouling. As a result, in the presence of fouling, the measured ratio $R_{measured}$ will be larger than $R_{true}$:

$$\frac{q}{i_{ss}(\text{measured})} = R_{measured} > R_{true} = \frac{q}{i_{ss}(\text{true})} \quad (1)$$

The reduced value of $i_{ss}$(measured) will cause the oxygen concentration of solution 16 to be underestimated. The predicted value of the steady state current ($i_{ss}$(true)), that is, the steady state current that would be measured in the absence of fouling, is restored from the measured value of q and the constant $R_{true}$, as follows:

$$i_{ss}(\text{true}) = \frac{q}{R_{true}} \quad (2)$$

Processor 32 uses the predicted value $i_{ss}$(true) in determining the oxygen concentration of solution 16. Alternatively, processor 32 compares the predicted value $i_{ss}$(true) to the measured value $i_{ss}$(measured) to generate a correction factor $\Delta i_{ss}$ for subsequent correction of the steady state current.

Referring to FIG. 10, processor 32 begins the error correction process each time a new sensor 11 is installed in analyzer 10, or when a previously fouled membrane 18 in sensor 11 is cleaned (step 300). After measurement electrode 12 of sensor 11 is energized, processor 32 waits until the current from electrode 12 reaches a steady state indicative of the oxygen concentration in solution 16 (step 302). This warmup or calibration period typically lasts about fifteen minutes. Analyzer 10 then enters a "learning mode" in which processor 32 calculates the value of $R_{true}$ characteristic of sensor 11 (step 304). During the learning mode, analyzer 10 measures the oxygen concentration by energizing measurement electrode 12 in a steady state manner. Periodically (e.g, every fifteen minutes to one hour), measurement electrode 12 is shut off, and test electrode 14 is energized in a pulse of approximately ten seconds to obtain a measurement of q. After six to eight values of q have been taken, processor 32 calculates and stores a value for $R_{true}$. Analyzer 10 then enters an operational mode, during which processor 32 continues to measure oxygen concentration by energizing measurement electrode 12 for a duration sufficient to cause electrode 12 to produce a steady-state signal, and continues to periodically energize (i.e., pulse) test electrode 14 (between energizations of measurement electrode 12) to check for fouling of membrane 18. During this stage, processor 32 performs the error correction (step 306).

It is not necessary that measurement electrode 12 be turned off while test electrode 14 is turned on. This is done solely for convenience in the instrumentation design. In practice, because the off time ($\Delta T$) of measurement electrode 12 is short compared to the fifteen minute or longer steady state readings, the steady state current $i_{ss}$ is quickly returned when measurement electrode 12 is turned back on. During the off time, the output of measurement electrode 12 is held and the correction is applied to the steady state current at the end of the test pulse.

Referring to FIG. 11, the learning mode typically takes place during the calibration of analyzer 10, described above in connection with FIG. 7. During calibration, sensor 11 is typically immersed in an air-saturated solution of known oxygen concentration.

In the learning mode, processor 32 begins by measuring the steady state current $i_{ss}$ from measurement electrode 12 (step 350). The steady state current is then sampled (step 352) and temperature corrected (step 354), as described above in connection with FIG. 5. Processor 32 then determines the oxygen concentration corresponding to the steady state current from calibration data 98 (FIG. 1), and displays this concentration to the user through user interface 35.

The oxygen concentration continues to be updated by analyzer 10 at a given rate, e.g., once per second, until a preset period of time $\Delta T$ has elapsed. Time $\Delta T$ is typically 20 minutes, but may be as long as one hour or more. After $\Delta T$ has elapsed (step 356), measurement electrode 12 is turned off, and test electrode 14 is pulsed in its place for ten seconds, as discussed above (step 358). The resulting test electrode current within the two-to-four second window during the pulse is sampled (step 360) and temperature corrected (step 362). These samples are then integrated to produce a measured value of q, i.e., the integral of current with respect to time is calculated (step 364), and the value of q is stored. Processor 32 next calculates $R_{measured}$ by dividing q by the last measured value of $i_{ss}$ (step 368).

Processor 32 then checks whether a selected number N of values of $R_{measured}$ have been measured, where N is typically between 6 and 10 (step 370). If N values of $R_{measured}$ have not yet been obtained, measurement electrode 12 is reenergized, and the process repeats. Once N values of $R_{measured}$ have been measured, processor 32 averages the values of $R_{measured}$ to produce a precise estimate of $R_{true}$ for newly installed (or newly cleaned) sensor 11 (step 372). Before exiting the learning mode, processor 32 initializes a correction factor $\Delta i_{ss}$ (subsequently used in the operation mode) to zero (step 374).

The learning mode thus continues for 2 to 10 hours (depending on the values of N and $\Delta T$) after sensor 11 has been cleaned or installed. This is typically much shorter than the time required for membrane 18 to become fouled (which generally occurs over a period of several days or longer). As a result, no error corrections are made during this stage.

Figures 12, 13:
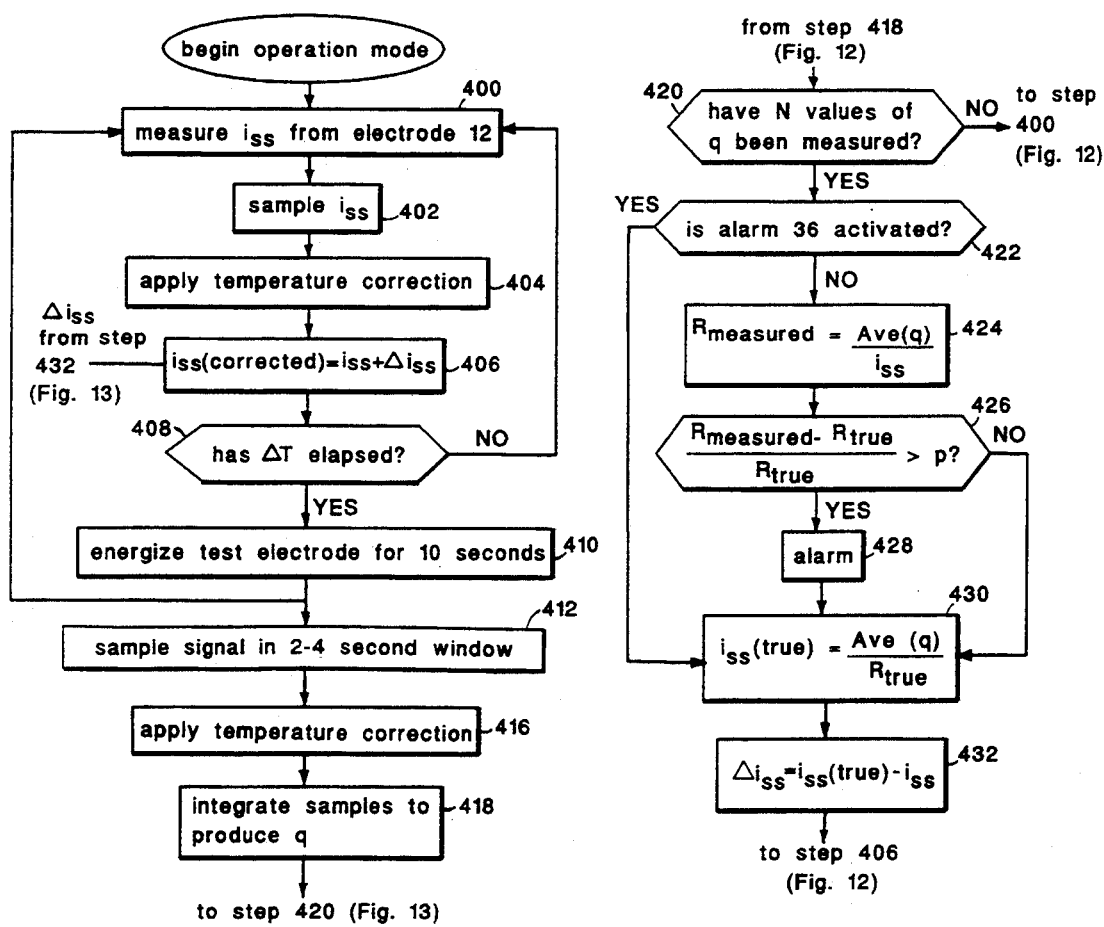
FIGS. 12 and 13 are flowcharts of the "operation mode" step shown in FIG. 10.

Referring to FIGS. 12 and 13, analyzer 10 next enters the operational mode, in which $i_{ss}$ continues to be measured (step 400), sampled (step 402) and temperature corrected (step 404), all as discussed above. Processor 32 then applies correction factor $\Delta i_{ss}$ to the measured value of $i_{ss}$ to produce a corrected value $i_{ss}$(corrected) (step 406). Initially, before any fouling has occurred, $\Delta i_{ss}$ is zero (as set in step 374 of the learning mode) and the value of $i_{ss}$ is not changed in step 406. After fouling has occurred, a non-zero value for $\Delta i_{ss}$ is calculated in step 432, discussed below, and is added to $i_{ss}$ in step 406 to compensate for the decrease in $i_{ss}$ caused by the fouling. An accurate measure of the true oxygen concentration of solution 16 is thus produced from the corrected value $i_{ss}$(corrected).

After $\Delta T$ has elapsed (step 408), analyzer 10 energizes test electrode 14 (step 410), and samples the test electrode current within the 2 to 4 second window after electrode 14 has been energized (step 412). After ten seconds, test electrode 14 is turned off, measurement electrode 12 is re-activated, and analyzer 10 continues to determine a value of the oxygen concentration from the measured and corrected value of $i_{ss}$.

At the same time, processor 32 temperature corrects the sampled signal (step 416), and integrates the signal to produce a measured value of q (step 418). After N values of q have been calculated (step 420), processor 32 begins a series of steps to determine whether fouling has occurred, and to calculate the value of $\Delta i_{ss}$ required to correct the value of the steady state current in step 406. N is typically chosen between six and eight, so that the required number of values of q will have been accumulated in the learning mode. Processor 32 will thus perform steps 422–432 after the first test electrode pulse, and each subsequent test electrode pulse, of the operational mode.

In step 422, processor 32 checks whether fouling has been previously detected, as indicated by an activated alarm 36. (The alarm may be activated as shown in FIG. 5, or in the alternative way shown in FIG. 13 and discussed below). The first time processor 32 enters step 422, alarm 36 will not have been activated, and processor 32 must check whether fouling has occurred. This is done by averaging the six to eight values of q to reduce measurement error, and by calculating $R_{measured}$ by dividing the averaged value of q by the last measured value of $i_{ss}$ (step 424). $R_{measured}$ is then compared to $R_{true}$ (step 426). If $R_{measured}$ exceeds $R_{true}$ by a threshold equal to a given fraction (p) of $R_{true}$, say 30%, alarm 36 is activated to indicate the presence of fouling (step 428).

After alarm 36 has been activated, a predicted value $i_{ss}$(true) for $i_{ss}$ is calculated by dividing the averaged value of the last six measurements of q by the value of $R_{true}$ (step 430). (The average is thus a "running" average of the last six stored values of q.) The difference between $i_{ss}$(true) and the last measured value of $i_{ss}$ provides the correction factor $\Delta i_{ss}$ (step 432), which is subsequently used in step 406 to correct the value of $i_{ss}$. As discussed in more detail below, the value of $\Delta i_{ss}$ remains unchanged for the subsequent measurement period $\Delta T$. $\Delta i_{ss}$ is recalculated (and possibly changed) after the next test electrode pulse.

If, in step 426, $R_{measured}$ differs from $R_{true}$ by less than the fraction p, the process skips ahead to step 430, and calculates $\Delta i_{ss}$ without activating alarm 36. The value of $i_{ss}$ is thus corrected even for a relatively small amount of fouling of membrane 18. This results in a precise and gradual adjustment of the steady state current.

After test electrode 14 has been pulsed a second time, processor 32 returns to step 422 to check whether alarm 36 was activated after the previous test pulse. If alarm 36 was activated, there is no need for processor 32 to recalculate $R_{measured}$ to determine whether fouling has occurred. Consequently, processor 32 jumps ahead to step 430 to calculate $i_{ss}$(true) from $R_{true}$ and the average of the last six values of q.

The averaged value of q used in the error correction scheme described above is useful when the oxygen concentration of solution 16 does not vary significantly over the time needed for six to eight samples of q to be collected (although q is independent of fouling, it does depend on oxygen concentration). Otherwise, the value of $i_{ss}$(true) determined from the averaged value of q will be erroneous. In this case, $R_{measured}$ should instead be calculated individually for each measurement of q and the corresponding, last measured $i_{ss}$. The values of $R_{measured}$ would then be averaged, and compared to $R_{true}$ to determine if fouling has occurred. The corrected steady state current $i_{ss}$(corrected) would then be found separately for each measured value of q.

The error correction scheme described above provides a linear correction factor $\Delta i_{ss}$ for the steady state current. For the next twenty minute period before test electrode 14 is re-energized, this correction factor remains constant. Because fouling is typically a very slow process, updating $i_{ss}$ once every 20 minutes is generally more than sufficient to correct for fouling effects. Variations in $i_{ss}$ during the twenty minutes between updates are likely to be due to changes in the oxygen concentration of the solution, rather than fouling.

If, however, it is found than the effects of fouling are occurring more rapidly than changes in the oxygen concentration, $\Delta i_{ss}$ should be increasing within the twenty minutes when analyzer 10 is not being tested. In this scenario, $i_{ss}$(true) provides a more accurate reading for $i_{ss}$ than $i_{ss}+\Delta i_{ss}$. Processor 32 can thus simply replace $i_{ss}$ with $i_{ss}$(true) without performing step 406 for the entire time $\Delta T$ between test electrode energization. Alternatively, other empirically determined correction factors can be used in place of $\Delta i_{ss}$.

The error correction scheme described above may be expressed in different ways. In essence, the scheme uses calibration data 98 to compensate for fouling (FIG. 1). For example, in an equivalent scheme, after each measurement of q, the corresponding value of oxygen concentration may be determined from total charge curve 150 (FIG. 7). This value may then be compared to the value of oxygen concentration determined from calibration curve 140 for $i_{ss}$. The discrepancy in the oxygen concentration may then used to subsequently correct for values of the concentration as read from the calibration curve for $i_{ss}$.

In a very simple scheme, only the oxygen concentration read from q calibration curve 150 could be used, because this measurement is unaffected by fouling. This technique is useful when the value of the measured oxygen concentration needs to be updated only very infrequently, i.e., once every 20 minutes or longer.

In addition, processor 32 could correct iss only when $R_{measured}$ varies from $R_{true}$ by a given percentage. This would save computations in processor 32. Also, processor 32 may stop correcting $i_{ss}$ when measurement errors in $i_{ss}$ and q are expected to be relatively large, e.g., when the oxygen concentration is below 5% of saturation (20.9%).

In other embodiments, the value of q used to calculate $i_{ss}$(true) in step 430 could be filtered in ways other than by performing an arithmetic average. For example, a time-weighted average may be used.

In still other embodiments, the error correction scheme shown in FIG. 13 could be modified to include activating alarm 36 if the correction factor $\Delta i_{ss}$ (which is indicative of the degree of fouling of membrane 18) exceeds a threshold. In this case, steps 424 and 426, in which $R_{measured}$ is calculated and compared to $R_{true}$ to determine whether alarm 36 should be activated, may be omitted.

Still other embodiments are within the scope of the following claims.

What is claimed is:

1. A method for detecting a selected chemical in a fluid with a device including an electrode assembly separated from said fluid by a membrane, comprising the steps of
    energizing said electrode assembly to generate a steady state signal that indicates a level of said selected chemical in said fluid and that is affected by fouling of said membrane, and a pulsed signal that indicates the level of said selected chemical in said fluid and that is substantially unaffected by fouling of said membrane,
    using said pulsed signal and said steady state signal to determine a value that said steady state signal will have in the absence of fouling of said membrane, and
    correcting said steady state signal based on said value to compensate for fouling of said membrane.

2. The method of claim 1 wherein said energizing includes energizing a measurement electrode to produce said steady state signal, and energizing a test electrode to produce said pulsed signal.

3. The method of claim 2 further comprising energizing said measurement electrode for a duration to allow said steady state signal to reach a steady-state value.

4. The method of claim 2 further comprising energizing said test electrode for a duration which does not allow said pulsed signal to reach a steady-state value.

5. The method of claim 4 further comprising energizing said test electrode for a duration that is shorter than a duration in which the measurement electrode is energized.

6. The method of claim 2 further comprising
    energizing said test electrode periodically to produce the steady state signal.

7. The method of claim 6 further comprising
    determining said value from the pulsed signal produced during a test electrode energization and the steady state signal produced by the measurement electrode, and
    using the value to correct the steady state signal produced after completion of the test electrode energization.

8. The method of claim 6 further comprising determining a correction factor from said value each time said test electrode is energized to produce said pulsed signal, and using said correction factor to correct said steady state current produced after completion of each test electrode energization.

9. The method of claim 2 further comprising energizing said measurement electrode and said test electrode for mutually exclusive intervals of time.

10. The method of claim 1 further comprising measuring a calibration pulsed signal and a calibration steady state signal while said membrane is unaffected by fouling, and determining said value from said pulsed signal, said calibration pulsed signal, and said calibration steady state signal.

11. The method of claim 10 further comprising integrating the calibration pulsed signal and the pulsed signal over time to determine said value.

12. The method of claim 11 further comprising
    measuring a plurality of pulsed signals,
    integrating each pulsed signal,
    determining an average of the integrated pulsed signals, and
    determining said value from said average of the integrated pulsed signals, the calibration pulsed signal, and the calibration steady state signal.

13. The method of claim 11 further comprising integrating the pulsed signal and the calibration pulsed signal over an identical time window during energization of the test electrode.

14. The method of claim 13 wherein the time window is shorter than a duration of the pulsed signal and a duration of the calibration pulsed signal.

15. The method of claim 11 further comprising determining said value by causing a ratio of the integrated pulsed signal to said value to be equal to a ratio of the integrated calibration pulsed signal to the calibration steady state signal.

16. The method of claim 11 further comprising measuring a plurality of calibration pulsed signals, integrating each calibration pulsed signal, determining ratios of the integrated calibration pulsed signals to the calibration steady state signal, determining an average of the calculated ratios, wherein said value is determined from the integrated pulsed signal and the average of the calculated ratios.

17. The method of claim 1 further comprising comparing said value to said steady state signal to produce a correction factor, and applying said correction factor to correct said steady state signal.

18. The method of claim 17 further comprising determining said correction factor based on a difference between the value and the steady state signal.

19. The method of claim 1 further comprising correcting said steady state signal by substituting said value for said steady state signal.

20. The method of claim 1 further comprising determining whether said membrane has been fouled to a given extent, and, if so, activating an alarm.

21. The method of claim 20 further comprising determining whether a difference between said value and said steady state signal exceeds a threshold, and determining that said membrane is fouled to said given extent if said difference exceeds said threshold.

22. The method of claim 20 further comprising measuring a calibration pulsed signal and a calibration steady state signal while said membrane is unaffected by fouling, integrating an amplitude of said pulsed signal and said calibration pulsed signal over time, comparing a calibration ratio of the integrated calibration pulsed signal to the calibration steady signal to a measurement ratio of the integrated pulsed signal to the steady state signal, and determining that said membrane has been fouled to said given extent if said measurement ratio differs from said calibration ratio by more than a threshold.

23. The method of claim 1 further comprising determining the level of the selected chemical in the fluid from the corrected steady state signal.

24. The method of claim 23 further comprising correcting a subsequent measurement of the steady state signal only if said level exceeds a threshold.

25. Apparatus for detecting a selected chemical in a fluid, comprising
an electrode assembly,
a membrane separating said electrode assembly from said fluid,
a power source for energizing said electrode assembly to generate a steady state signal that indicates a level of said selected chemical in said fluid and that is affected by fouling of said membrane, and a pulsed signal that indicates the level of said selected chemical in said fluid and that is substantially unaffected by fouling of said membrane,
a processor responsive to said pulsed signal and said steady state signal for determining a value that said steady state signal will have in the absence of fouling of said membrane, and for correcting said steady state signal based on said value to compensate for fouling of said membrane.

26. The apparatus of claim 25 wherein said electrode assembly comprises
a measurement electrode for producing said steady signal, and
a test electrode for producing said pulsed signal.

27. The apparatus of claim 26 wherein said power source energizes said measurement electrode for a duration to allow said steady state signal to reach a steady-state value.

28. The apparatus of claim 25 wherein said power source energizes said test electrode for a duration which does not allow said pulsed signal to reach a steady-state value.

29. The apparatus of claim 25 further comprising a controller for causing said power source to continually energize the measurement electrode and to periodically energize the test electrode.

30. The apparatus of claim 29 wherein said processor determines said value from the pulsed signal produced during a test electrode energization and the steady state signal produced by the measurement electrode, the value being used to correct the steady state signal produced after completion of the test electrode energization.

31. The apparatus of claim 29 wherein the processor determines a correction factor from said value each time said power source energizes said test electrode to produce said pulsed signal, said processor using said correction factor to correct said steady state current produced after completion of each test electrode energization.

32. The apparatus of claim 26 wherein the controller causes the power source to energize the test electrode and the measurement electrode for mutually exclusive intervals of time.

33. The apparatus of claim 25 wherein said processor comprises storage for a calibration pulsed signal and a calibration steady state signal produced by said test electrode and said measurement electrode while said membrane is unaffected by fouling, said processor determining said value from said pulsed signal, said stored calibration pulsed signal, and said stored calibration steady state signal.

34. The apparatus of claim 33 wherein the processor integrates the calibration pulsed signal and the pulsed signal over time prior to determining said value.

35. The apparatus of claim 34 wherein the processor integrates each of a plurality of pulsed signals before determining an average of the integrated pulsed signals, the processor determining said value from said average of the integrated pulsed signals, the stored calibration pulsed signal, and the stored calibration steady state signal.

36. The apparatus of claim 34 wherein the processor integrates the pulsed signal and the calibration pulsed signal over the same time window during test electrode energization.

37. The apparatus of claim 36 wherein the time window is shorter than a duration of the pulsed signal and a duration of the calibration pulsed signal.

38. The apparatus of claim 34 wherein the processor determines said value by causing a ratio of said value to the integrated pulsed signal to be equal to a ratio of the calibration steady state signal to the integrated calibration pulsed signal.

39. The apparatus of claim 34 further comprising a controller for causing the power source to energize the measurement electrode continuously and the electrode assembly periodically while the membrane is unaffected by fouling to generate calibration pulsed signals and the calibration steady state signal, the processor determining said value by calculating ratios of the integrated calibration pulsed signals to the calibration steady state signal, and using the integrated pulsed signal and the average of the calculated ratios to determine said value.

40. The apparatus of claim 25 wherein the processor compares said value to said steady state signal to produce a correction factor used to correct said steady state signal.

41. The apparatus of claim 40 the processor determines a difference of the value and the steady state signal to produce said correction factor.

42. The apparatus of claim 25 wherein the processor corrects said steady state signal by substituting said value for said steady state signal.

43. The apparatus of claim 25 wherein said processor determines whether said membrane has been fouled to a given extent, and, if so, activates an alarm.

44. The apparatus of claim 43 wherein said processor determines whether a difference between said value and said steady state signal exceeds a threshold and determines that the membrane has been fouled to said given extent when said difference exceeds said threshold.

45. The apparatus of claim 43 further comprising a controller for causing the power source to energize the measurement electrode and the test electrode while the membrane is unaffected by fouling to produce a calibration pulsed signal and a calibration steady state signal, said processor integrating said pulsed signal and said calibration pulsed signal over time and comparing a calibration ratio of the integrated calibration pulsed signal to the calibration steady signal to a measurement ratio of the integrated pulsed signal to the steady state signal, said processor determining that said membrane has been fouled to said given extent if said measurement ratio differs from said calibration ratio by more than a threshold.

46. The apparatus of claim 25 wherein the processor determines the level of the selected chemical in the fluid from the corrected steady state signal.

47. The apparatus of claim 25 wherein the processor corrects a subsequent measurement of the steady state signal only if said level exceeds a given threshold.

* * * * *